United States Patent
Chattaraj et al.

(10) Patent No.: US 8,722,083 B2
(45) Date of Patent: May 13, 2014

(54) FENOFIBRATE FORMULATION

(75) Inventors: Sarat C. Chattaraj, Morgantown, WV (US); Glenn Allen Redelman, Morgantown, WV (US); Andrew Alan Shaw, Morgantown, WV (US)

(73) Assignee: Mylan, Inc., Morgantown, WV (US)

( * ) Notice: Subject to any disclaimer, the term of this patent is extended or adjusted under 35 U.S.C. 154(b) by 0 days.

(21) Appl. No.: 13/531,955

(22) Filed: Jun. 25, 2012

(65) Prior Publication Data

US 2013/0344155 A1 Dec. 26, 2013

(51) Int. Cl.
- *A61K 9/54* (2006.01)
- *A61K 9/26* (2006.01)
- *A61K 9/16* (2006.01)
- *A61K 31/19* (2006.01)

(52) U.S. Cl.
USPC ............ 424/458; 424/470; 424/494; 514/571

(58) Field of Classification Search
USPC ........................... 424/458, 470, 494; 514/571
See application file for complete search history.

(56) References Cited

U.S. PATENT DOCUMENTS

| | | |
|---|---|---|
| 4,800,079 A | 1/1989 | Boyer |
| 6,696,084 B2 | 2/2004 | Pace et al. |
| 7,037,529 B2 | 5/2006 | Stamm et al. |
| 7,041,319 B2 | 5/2006 | Stamm et al. |
| 7,101,574 B1 | 9/2006 | Criere et al. |
| 7,863,331 B2 | 1/2011 | Criere et al. |
| 2003/0077297 A1 | 4/2003 | Chen et al. |
| 2004/0091535 A1 | 5/2004 | Vachon et al. |
| 2008/0063726 A1 | 3/2008 | Stamm et al. |
| 2008/0131503 A1 | 6/2008 | Holm et al. |
| 2008/0241070 A1 | 10/2008 | Ryde et al. |
| 2009/0028941 A1 | 1/2009 | Cowles et al. |
| 2009/0035379 A1 | 2/2009 | Stamm et al. |
| 2010/0166857 A1* | 7/2010 | Yan et al. ...................... 424/465 |
| 2011/0311619 A1 | 12/2011 | Herry et al. |
| 2011/0311625 A1 | 12/2011 | Doddaveerappa et al. |

FOREIGN PATENT DOCUMENTS

| | | |
|---|---|---|
| EP | 0256933 | 2/1988 |
| EP | 0330532 | 8/1989 |

OTHER PUBLICATIONS

Wolff, Manfred E. ("Burger's Medicinal Chemistry, 5ed, Part I", John Wiley & Sons, 1995, pp. 975-977.*
Banker, G.S. et al. ("Modern Pharmaceutics, 3ed.", Marcel Dekker, New York, 1996, pp. 451 and 596.*
International Search Report dated Aug. 31, 2012 for PCT/US2012/043971.
International Search Report dated Dec. 28, 2012 for PCT/US2012/061486.

(Continued)

*Primary Examiner* — Aradhana Sasan
(74) *Attorney, Agent, or Firm* — Kramer Amado, P.C.

(57) ABSTRACT

Various fenofibrate compositions include a plurality of first granules having a high bioavailability in vivo, and a plurality of second granules having a low bioavailability in vivo. The first granules may comprise fenofibrate, from 0.3% to 10% by weight of the first granules of a first surfactant, and a first water soluble or water dispersible cellulose derivative, and the second granules may comprise fenofibrate, from 0% to 0.25% by weight of the second granules of a second surfactant, and a second water soluble or water dispersible cellulose derivative.

20 Claims, 3 Drawing Sheets

(56) References Cited

OTHER PUBLICATIONS

Siepman, et al., "Hydrophilic matrices for Controlled Drug Delivery: An Improved Mathematical Model to Predict the REsultring Drug Release Kinetics (the "Sequential layer" Model)", Pharmaceutical Research, vol. 17, No. 10, 2000, 190-1298.

Sornay, et al., "Antilipidemic Drugs", Arzneim Forsh (Drug Res.) 26, Nr. 5 (1976), 885-889.

\* cited by examiner

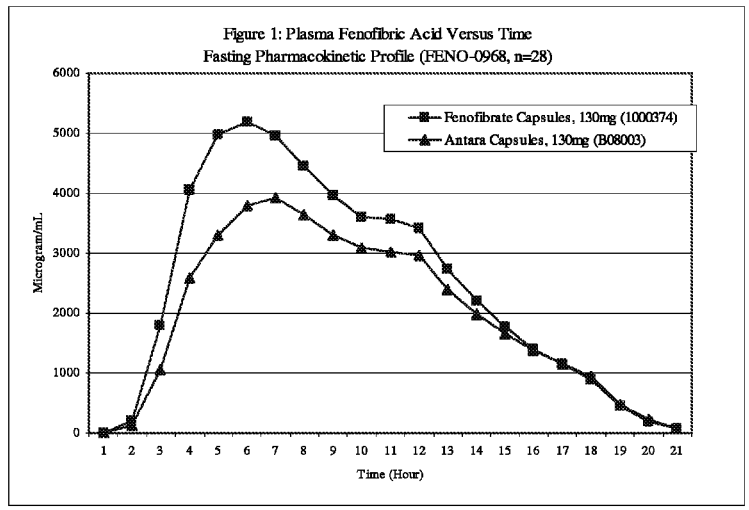
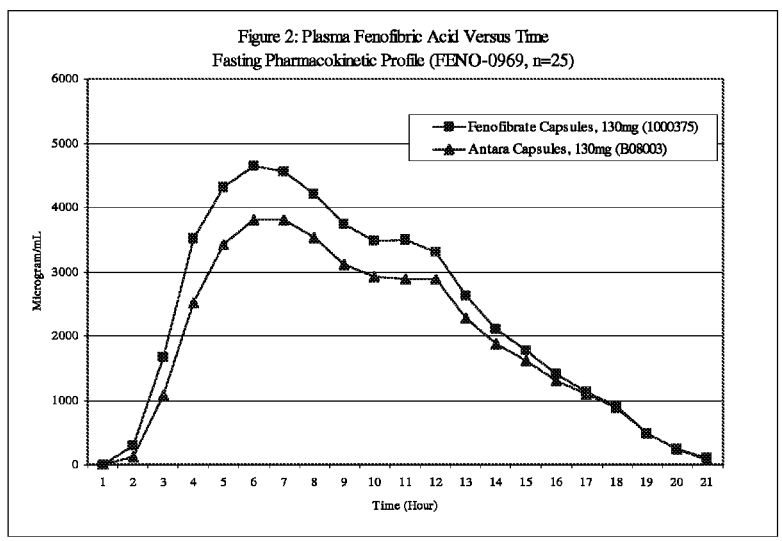

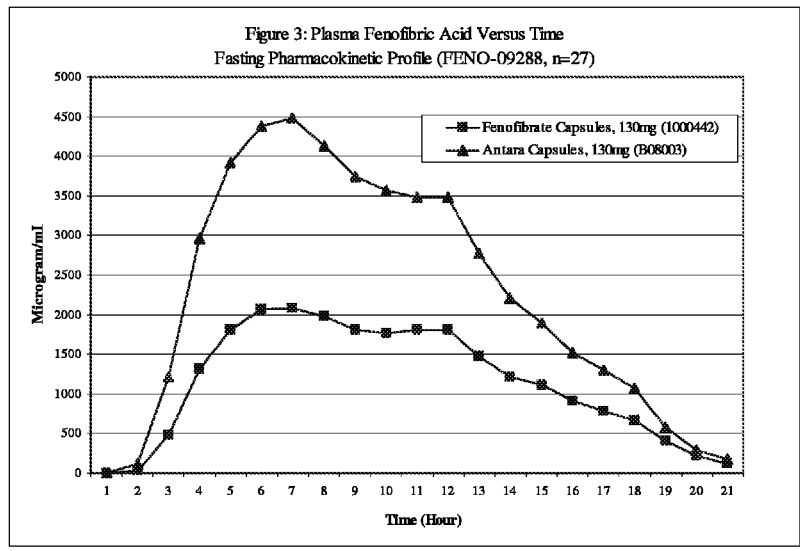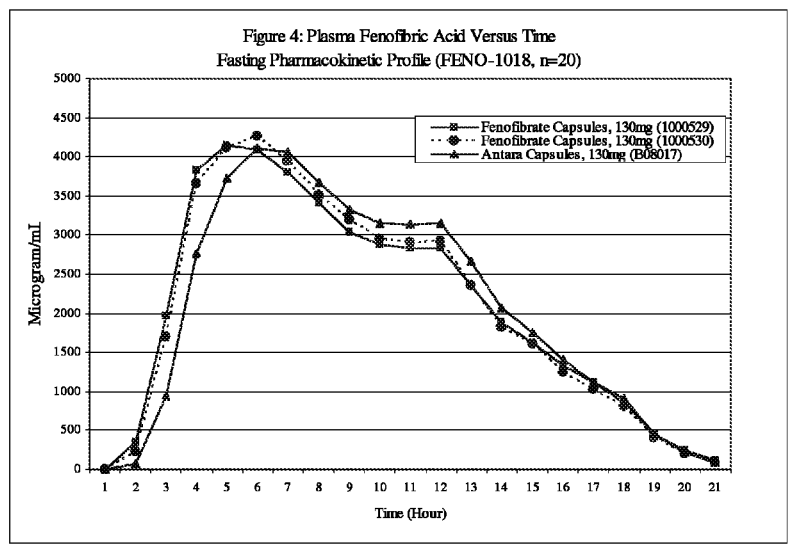

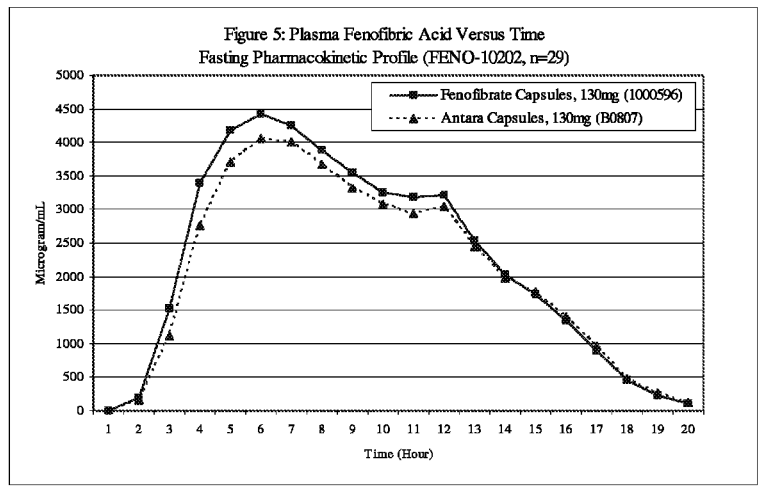
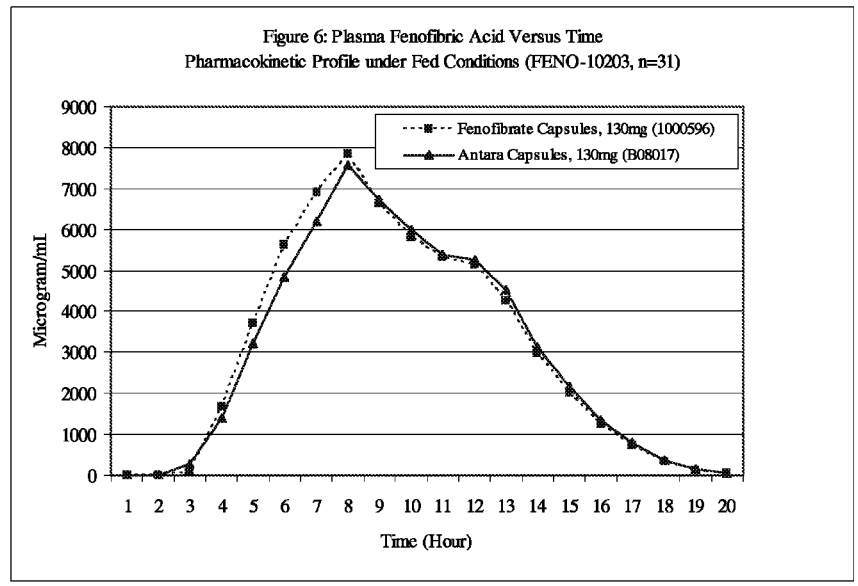

FENOFIBRATE FORMULATION

BACKGROUND

1. Field of the Invention

This invention relates generally to immediate release fenofibrate dosage forms.

2. Description of Related Art

Fenofibrate is an active principle which is very poorly soluble in water, and the absorption of fenofibrate in the digestive tract is limited. An increase in its solubility leads to better digestive absorption. Various approaches have been explored in order to increase the solubility of fenofibrate, including micronization of the active principle, addition of a surfactant, and comicronization of fenofibrate with a surfactant.

Fenofibrate is freely soluble in methanol and acetonitrile, and insoluble in water. Having no ionizable group, fenofibrate solubility is not influenced by changes in medium pH. However, the aqueous solubility of Fenofibrate can be improved in the presence of surfactants. As the concentration of the surfactant sodium lauryl sulfate, for example, increases from 0.0 M to 0.1M, fenofibrate solubility increases from 0.8 mg/L to 910.8 mg/L.

U.S. Pat. No. 4,800,079 (Jan. 24, 1989, Jean-Francois Boyer) describes a granular medicine based on fenofibrate, each granule comprising an inert core, a layer based on fenofibrate, and a protective layer. The medicine is characterized in that the fenofibrate is present in the form of crystalline microparticles having a size of less than 30 microns, and preferably less than 10 microns. The layer based on fenofibrate includes a binder selected from the group consisting of methacrylic polymers, polyvinylpyrolidone, cellulose derivatives, and polyethylene glycols.

U.S. Pat. No. 7,101,574 (Sep. 5, 2006, Bruno Criere et. al.) describes a pharmaceutical composition containing micronized fenofibrate, a surfactant and a cellulose derivative as a binder, preferably hydroxypropylmethylcellulose. The cellulose derivative represents less than 20 wt. % of the composition, while the fenofibrate is present in an amount greater than or equal to 60% by weight of the pharmaceutical composition. The disclosed formulation provides enhanced bioavailability of the active principle.

EP Patent 0256933 describes fenofibrate granules containing micronized fenofibrate to increase fenofibrate bioavailability. The fenofibrate microparticles are less than 50 micron in size, and polyvinylpyrrolidone is used as a binder. The document describes other types of binder, such as methacrylic polymers, cellulose derivatives and polyethylene glycols.

EP Patent 0330532 describes improving the bioavailability of fenofibrate by comicronizing it with a surfactant, such as sodium lauryl sulfate. The comicronized product is then granulated by wet granulation in order to improve the flow capacities of the powder and to facilitate the transformation into gelatin capsules. This comicronization allows a significant increase in the bioavailability compared to the use of fenofibrate described in EP 0256933. The granules described in EP 0330532 contain polyvinylpyrrolidone as a binder. EP 0330532 teaches that the comicronization of fenofibrate with a solid surfactant improves the bioavailability of fenofibrate compared to either micronized fenofibrate, or to the combination of a surfactant and of micronized fenofibrate. However, the formulation of EP 0330532 is unsatisfactory, as it does not provide complete bioavailability of the active ingredient. The technique of co-micronizing fenofibrate with a solid surfactant improves dissolution of fenofibrate, but still produces incomplete dissolution.

SUMMARY

A summary of various embodiments is presented herein. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections. Various embodiments disclosed herein relate to a dosage form comprising an effective amount of fenofibric acid, pharmaceutically acceptable salts thereof, pharmaceutically acceptable esters thereof, or prodrugs thereof. In various embodiments, the active agent is fenofibrate, an ester of fenofibric acid which is hydrolyzed to fenofibric acid in vivo. Fenofibrate is a prodrug of fenofibric acid.

In the present disclosure, a fenofibrate formulation comprises a population of low bioavailability fenofibrate-containing beads (slow beads), and a population of high bioavailability fenofibrate-containing beads (fast beads). A portion of the desired fenofibrate dose is included in the slow beads, and the remainder of the desired fenofibrate dose is included in the fast beads. The fast and slow beads are combined to produce a single dosage form having a desired bioavailability, as measured by the rate and extent of absorption. Specifically, the rate and extent of absorption is measured by the parameters AUCL, AUCI, and Cpeak. The parameter AUCL is the area under the plasma concentration-time curve from time zero to time t, where t is the last time point with measurable concentration for individual formulation. The parameter AUCI is the area under the plasma concentration-time curve from time zero to time infinity. Additionally, Cpeak is the maximum plasma concentration of the drug.

Where the bioavailability of the population of high bioavailability fenofibrate-containing beads is higher than desired, the overall bioavailability of the dosage form may be modulated by the presence of low bioavailability fenofibrate-containing beads.

In various embodiments, the dosage form comprises a plurality of first granules and a plurality of second granules combined in a weight ratio of said first granules to said second granules of between about 50:50 and about 90:10, where the dosage form provides a peak plasma concentration of fenofibric acid of between 4000 ng/mL and 4800 ng/mL fenofibrate when administered to a human subject. In contrast, a first comparative dosage form comprising 100% of first granules provides a peak plasma concentration of fenofibric acid of greater than 4800 ng/mL, when administered to a human subject; and a second comparative dosage form comprising 100% of second granules provides a peak plasma concentration of fenofibric acid of less than 3500 ng/mL when administered to a human subject.

Various embodiments relate to a pharmaceutical composition having a target bioavailability in vivo, where the pharmaceutical composition comprises a plurality of first granules having a first bioavailability in vivo, and a plurality of second granules having a second bioavailability in vivo which is less than said first bioavailability, said target bioavailability being between said first bioavailability and said second bioavailability. The first granules comprise fenofibrate, a first surfactant, and a first water soluble or water dispersible cellulose derivative; and said second granules comprise fenofibrate; an optional second surfactant; and a second water soluble or water dispersible cellulose derivative. In various embodiments, the pharmaceutical composition comprises from 50% to 90% of the first granules, based on the combined weight of the first and second granules; and from 10% to 50% of the second granules, based on the combined weight of the first and second granules. The pharmaceutical composition may comprise at least one pharmaceutically inactive excipient or additive, in addition to the first and second granules.

In various embodiments, the first bioavailability in vivo is the bioavailability of a comparative dosage form comprising 100% of said first granules and 0% of said second granules; and the second bioavailability in vivo is the bioavailability of a comparative dosage form comprising 0% of said first granules and 100% of said second granules.

Various embodiments relate to an immediate release pharmaceutical composition comprising a plurality of first granules comprising a first composition, where the first composition includes fenofibrate, from 0.3% to 10% by weight of the first granules of a first surfactant, and a first water soluble or water dispersible cellulose derivative; and a plurality of second granules comprising a second composition including fenofibrate, from 0% to 0.25% by weight of the second granules of a second surfactant, and a second water soluble or water dispersible cellulose derivative. The first composition releases fenofibrate at a first rate upon exposure to water; and the second composition releases fenofibrate at a second rate upon exposure to water, said second rate being less than said first rate. In various embodiments, each first granule comprises an inert core coated with a layer of the first composition; and each second granule comprises an inert core coated with the second composition.

Various embodiments disclosed herein relate to a pharmaceutical composition comprising a plurality of first granules having a first coating, where the first coating has a high bioavailability in vivo, in combination with a plurality of second granules having a second coating, where the second coating has a low bioavailability in vivo. The first coating comprises fenofibrate, from 0.3% to 10% by weight of said first granules of a first surfactant, and a first water soluble or water dispersible cellulose derivative, while the second coating comprising fenofibrate, from 0% to 0.25% by weight of said second granules of a second surfactant, and a second water soluble or water dispersible cellulose derivative. In some embodiments, the first coating comprises from 0.3% to 10% by weight of the first granules of the first surfactant, and the second coating comprises from 0% to 0.05%, preferably 0%, by weight of the second granules of the second surfactant.

According to various embodiments described herein, the first surfactant is the same as the second surfactant. In other embodiments, the first surfactant is different from the second surfactant. Similarly, the first cellulose derivative and the second cellulose derivative may be the same or different. The first and second surfactants may be anionic surfactants, non-ionic surfactants, or cationic surfactants, preferably anionic surfactants. A preferred surfactant is sodium lauryl sulfate.

Various embodiments disclosed herein relate to a pharmaceutical composition comprising a plurality of first coated granules, where each first coated granule includes a first inert core coated with a first composition comprising fenofibrate and a first water soluble or water dispersible cellulose derivative. The fenofibrate and the first cellulose derivative are present in said first composition in a weight ratio of from about 1:1 to less than 5:1. The pharmaceutical composition additionally comprises a plurality of second coated granules, each second granule including a second inert core coated with a second composition comprising fenofibrate and a second water soluble or water dispersible cellulose derivative, where the fenofibrate and the second cellulose derivative are present in a weight ratio of from greater than 5:1 to about 15:1.

In various embodiments, the fenofibrate and the first cellulose derivative are present in the first composition in a weight ratio of from about 2:1 to about 4.5:1, preferably from about 3.5:1 to about 4.5:1; and the fenofibrate and the second cellulose derivative are present in the second composition in a weight ratio of from about 6:1 to about 12:1, preferably from about 7:1 to about 9:1.

Various embodiments disclosed herein relate to a dosage form which is bioequivalent to ANTARA® capsules having an equivalent amount of fenofibrate. The bioequivalent dosage form comprising a defined amount of fenofibrate, which may be between 40 and 200 mg fenofibrate, preferably between 40 and 160 mg micronized fenofibrate. The dosage form comprises a first composition and a second composition being combined in a weight ratio of said first composition to said second composition of between about 50:50 and about 90:10, preferably between 60:40 and 90:10, most preferably between about 75:25 and 80:20. In various embodiments, the first composition has a high bioavailability and the second composition has a low bioavailability.

The standards for bioequivalence depend on several natural log transformed parameters associated with the rate and extent of absorption. Specifically, bioequivalence depends on the parameters AUCL and AUCI. The parameters AUCL and AUCI must fall between 80 and 125% of the corresponding values for the branded product for therapeutic equivalence. Additionally, the maximum plasma concentration, Cpeak, must fall between 80% and 125% of the corresponding Cpeak of the branded product for therapeutic equivalence.

The bioequivalent dosage form disclosed herein, containing the first composition and the second composition, when administered to a human subject, provides a peak plasma concentration Cpeak of fenofibric acid which is between 80% and 125% for the 90% confidence interval for Cpeak value obtained with ANTARA® capsules having an equivalent amount of fenofibrate. In various embodiments, a first comparative dosage form comprising 100% of the first composition provides a Cpeak of fenofibric acid which is between 105% and 160% of a Cpeak value obtained with said ANTARA® capsules, within a 90% confidence interval; while a second comparative dosage form comprising 100% of said second composition provides a Cpeak of fenofibric acid of less than 80% of a Cpeak value obtained with said ANTARA® capsules, within a 90% confidence interval.

In some embodiments, the first comparative dosage form comprising 100% of said first composition provides a Cpeak of fenofibric acid which is between 105% and 140% for the 90% confidence interval for Cpeak value obtained with said ANTARA® capsules, and the second comparative dosage form comprising 100% of said second composition provides a Cpeak of fenofibric acid of between 40% and 80% for the 90% confidence interval for Cpeak value obtained with said ANTARA® capsules. In various embodiments, the dosage form, when administered to a human subject, provides a value of AUCL for fenofibric acid which is between 80% and 125% for the 90% confidence interval for AUCL value obtained with the ANTARA® capsules having an equivalent amount of fenofibrate, and a value of AUCI for fenofibric acid which is between 80% and 125% for the 90% confidence interval for AUCI value obtained with the ANTARA® capsules having an equivalent amount of fenofibrate.

Various embodiments disclosed herein relate to the manufacture of Fenofibrate Capsules containing between 40 mg and 200 mg fenofibrate, preferably between 40 mg and 160 mg micronized fenofibrate. The manufacture of Fenofibrate Capsules involves manufacture of Fenofibrate Intermediate Beads having a slow drug release rate via rotor drug layering of an aqueous suspension of HPMC and fenofibrate particles onto inert core material, followed sequentially by fluidized bed drying, and screening the coated core material to control particle size. The ratio of drug to HPMC in these slow release beads is 8:1; the slow release beads do not contain surfactant.

The manufacture of Fenofibrate Capsules further involves manufacture of Fenofibrate Intermediate Beads having a fast drug release rate via rotor drug layering of an aqueous suspension of HPMC and fenofibrate particles onto inert core material, followed sequentially by fluidized bed drying, and screening the coated core material to control particle size. The ratio of drug to HPMC in these fast release beads is 4:1; the fast release beads contain between about 0.5% and about 2% by weight, based on the weight of the fast release beads, of a surfactant, preferably a sodium lauryl sulfate surfactant.

Fenofibrate Capsules are produced by combining the fast release beads and the slow release beads to form a mixture, and encapsulating the mixture in a gelatin capsule shell. Alternatively, Fenofibrate Capsules may be produced by introducing the fast release beads and the slow release beads into a gelatin capsule shell separately, e.g., by first introducing the fast release beads into the capsule shell, and then introducing the slow release beads into the capsule shell.

In various embodiments, the fast and slow release drug layered beads produced by the methods disclosed herein are free of agglomeration; achieve acceptable capsule content uniformity and potency; achieve rapid drug release from the dosage form; and achieve adequate chemical stability throughout the intended shelf life.

BRIEF DESCRIPTION OF THE DRAWINGS

In order to better understand various exemplary embodiments, reference is made to the accompanying drawings, wherein:

FIG. 1 and FIG. 2 show the concentration of fenofibrate in plasma over time upon administration of 130 mg ANTARA® capsules and administration of 130 mg capsules according to Example 4.

FIG. 3 shows the concentration of fenofibrate in plasma over time upon administration of 130 mg ANTARA® capsules and administration of 130 mg capsules according to Example 6.

FIG. 4 shows the concentration of fenofibrate in plasma over time upon administration of 130 mg ANTARA® capsules and administration of 130 mg capsules according to Example 7.

FIG. 5 and FIG. 6 show the concentration of fenofibrate in plasma over time upon administration of 130 mg ANTARA® capsules and administration of 130 mg capsules according to Example 8.

DETAILED DESCRIPTION

In certain embodiments, the high bioavailability fenofibrate-containing beads contain micronized fenofibrate, a surfactant, and a binder which is water-soluble or water-dispersible. Suitable binders include hydroxypropylmethylcellulose (HPMC); hydroxypropyl cellulose; hydroxyethyl cellulose; carboxymethylcellulose; povidone and chitosan, with HPMC being a preferred binder. A suitable HPMC binder is commercially available under the trade name Pharmacoat® 603, from Harke Group.

In certain embodiments, the low bioavailability fenofibrate-containing beads contain micronized fenofibrate, and a binder which is water-soluble or water-dispersible. Suitable binders include hydroxypropylmethylcellulose (HPMC); hydroxypropyl cellulose; hydroxyethyl cellulose; carboxymethylcellulose; povidone and chitosan, with HPMC being a preferred binder.

In various embodiments, the high bioavailability fenofibrate-containing beads contain a surfactant in an amount of between about 0.3% by weight and about 10% by weight, preferably between about 0.5% by weight and about 5% by weight, more preferably between about 0.5% by weight and about 3% by weight. The low bioavailability fenofibrate-containing beads contain a surfactant in an amount of between about 0% by weight and about 0.25% by weight, preferably between about 0% by weight and about 0.05% by weight, more preferably 0% by weight.

The low bioavailability fenofibrate-containing beads (slow beads) and the high bioavailability fenofibrate-containing beads (fast beads) may be co-administered in a single dosage form. The low bioavailability fenofibrate-containing beads and the high bioavailability fenofibrate-containing beads may be combined and filled into a hard gelatin shell to form a capsule.

Alternatively, they may be combined with a water-soluble or water-dispersible binder, and compressed along with tableting excipients to form an immediate-release solid oral dosage form such as a tablet. Such compressed tablets may include a combination of slow beads and fast beads mixed together and combined with the binder and excipients prior to compression. As an alternative, slow beads may be mixed with the binder and excipients prior to a first compression step to form a first layer containing slow beads; and then the fast beads may be combined with the binder and excipients prior to a second compression step. In the second compression step, the formulation of fast beads and binder is deposited on the first layer, and the formulation of fast beads is compressed to form a bilayer tablet. If desired, suitable colorants may be added to either or both of the slow bead formulation and the fast bead formulation so that the layers of the bilayer tablet are visually distinguishable. Alternatively, the formulation of fast beads may be compressed initially to form the first layer, with the second layer containing the formulation of slow beads.

In various embodiments, the fast beads and the slow beads may be combined, and then blended with suitable excipients, including a binder, a water-soluble or water-dispersible filler, a disintegrant and/or a lubricant. The resulting mixture may be compressed into multiple mini-tablets, which may then be then encapsulated in a suitable size two piece hard gelatin capsule shell.

In other embodiments, the fast beads may be blended with suitable excipients, and then compressed into multiple mini-tablets. Similarly, the slow beads may be blended with suitable excipients, and then compressed into multiple mini-tablets. Mini-tablets containing the fast beads may be mixed with mini-tablets containing the slow beads, and the resulting admixture may then be then encapsulated in a suitable size two piece hard gelatin capsule shell. In various embodiments, the mini-tablets containing the fast beads and the mini-tablets containing the slow beads contain equal amounts of fenofibrate, and are combined in a predetermined ratio. In various embodiments, a capsule containing mini-tablets containing fast beads and mini-tablets containing slow beads contains from 50% to 80% of mini-tablets containing fast beads and from 20% to 50% of mini-tablets containing the slow beads.

In various embodiments, the dosage of fenofibrate may take the form of multiple tablets to be coadministered. In various embodiments, a first tablet may contain fenofibrate in the form of fast beads only (a fast tablet), while a second tablet may contain fenofibrate in the form of slow beads only (a slow tablet). With this approach, one slow tablet may be coadministered with at least one fast tablet, preferably from one to three fast tablets.

In various embodiments, one tablet containing fast beads or a combination of slow and fast beads may be prepared as disclosed herein, and then combined with a granulated powder of fenofibrate and encapsulated in a suitable size two piece hard gelatin capsule shell. Alternatively, a combination of fast beads and granulated powder of fenofibrate can be encapsulated to achieve the desired drug release profile.

In various embodiments, the slow and fast beads can also be manufactured by extrusion spheronization technology. As an alternative to slow and fast beads, the dosage forms disclosed herein may be manufactured from granules manufactured by spray drying techniques. For example, a slurry of fenofibrate, a cellulosic binder, and a surfactant in an amount of between about 0.3% by weight and about 10% by weight, based on solids content, may be spray dried to form fast granules. A slurry of fenofibrate, a cellulosic binder, and a surfactant in an amount of between about 0% by weight and about 0.25% by weight, based on solids content, may be spray dried to form slow granules. The fast and slow granules may be used as substitutes for fast and slow beads.

In various embodiments, the fenofibrate beads or granules can be used for manufacturing combination pharmaceutical products. In some embodiments, the combination products may contain fenofibrate and a second drug, such as a statin, niacin, or metformin. The combination products may be manufactured by applying a fenofibrate suspension onto a core material, where the core material contains at least one pharmaceutical active, such as a statin, niacin, or metformin.

In some embodiments, the slow and fast beads may be combined and filled into a unit dose sealed pouch. The contents of the pouch may be dispersed in a liquid such as juice or water, and the patient may drink the resulting dispersion.

In various embodiments, the ratio of the fast and slow beads (fast beads:slow beads) in the dosage forms disclosed herein is between 50:50 and 90:10, preferably between 60:40 and 90:10, most preferably between about 75:25 and 80:20. The beads disclosed herein may be prepared by spraying the drug layer suspension onto inert cores, preferably inert cores having a 20 to 50 mesh particle size, i.e., 300 microns to 850 microns. In some embodiments, the inert cores may have a mesh size of 20 to 25, i.e., from 700 to 850 microns. In other embodiments, the inert cores may have a mesh size of 35 to 45, i.e., from 350 to 500 microns. In further embodiments, the fast beads may be made from inert cores having a mesh size of between 20 mesh and 25 mesh, while the slow beads may be made from inert cores having a mesh size of between 35 mesh and 45 mesh. In other embodiments, the fast beads may be made from 35 to 45 mesh cores, while the slow beads may be made from 20 to 25 mesh cores.

In one embodiment, an HPMC binder is solubilized in water or a polar organic solvent. Micronized fenofibrate is added to the binder solution to form a drug suspension. The surfactant is added to the drug suspension. Optionally, an antifoaming agent is incorporated into the drug suspension. Suitable antifoaming agents include silicones, such as dimethicone. Suitable solvents include Class 3 solvents, i.e., solvents of low toxic potential. Preferred Class 3 solvents include polar solvents suitable for dissolving or dispersing HPMC, such as water, Acetone, Anisole, 1-Butanol, 2-Butanol, 3-Methyl-1-butanol, Methyl ethyl ketone, Methyl isobutyl ketone, 2-Methyl-1-propanol, Dimethyl sulfoxide, Ethanol, 1-Pentanol, 1-Propanol, and 2-Propanol, and mixtures thereof. The resulting drug suspension is homogenized, and then sprayed onto the sugar spheres. In various embodiments, the drug suspension is homogenized for a minimum of 8 hours, preferably 8 to 48 hours, more preferably 8 to 24 hours, most preferably 8 to 10 hours, prior to spraying onto the inert cores.

In various embodiments, the beads disclosed herein may be prepared by spraying the drug layer suspension onto inert cores made from insoluble inert materials, such as silicon dioxide, calcium phosphate dihydrate, dicalcium phosphate, calcium sulfate dihydrate, microcrystalline cellulose, cellulose derivatives, calcium carbonate, dibasic calcium phosphate anhydrous, dibasic calcium phosphate monohydrate, tribasic calcium phosphate, magnesium carbonate, magnesium oxide and activated carbon. In various embodiments, the beads disclosed herein may be prepared by spraying the drug layer suspension onto soluble cores, such as sugar spheres, more particularly, spheres of sugars selected from the group consisting of like dextrose, lactose, anhydrous lactose, spray-dried lactose, lactose monohydrate, mannitol, starches, sorbitol, and sucrose. Other materials which may be used as inert cores include insoluble inert plastic materials, such as spherical or nearly spherical core beads of polyvinylchloride or polystyrene. Mixtures of these core materials may be used. In certain embodiments, low bioavailability fenofibrate-containing beads (slow beads) may be prepared using a different core material from high bioavailability fenofibrate-containing beads (fast beads).

In various embodiments, the drug suspension is sprayed onto the inert cores contains a surfactant. Suitable surfactants include anionic surfactants, nonionic surfactants, cationic surfactants, or mixtures thereof. Preferably, the surfactants are anionic surfactants. Suitable anionic surfactants include sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium lauryl sulfate; sodium undecane-3-sulfate, sodium ethylphenylundecanoate, and carboxylate soaps. Preferred anionic surfactants include C8 to C24 sulfate monoester surfactants. More preferred anionic surfactants include sodium 2-ethylhexyl sulfate, sodium lauryl sulfate; and sodium undecane-3-sulfate. Suitable cationic surfactants include benzalkonium halide salts. Suitable nonionic surfactants include C8-C28 ethoxylated alcohols, mono-, di-, and trimesters of glycerol, and Polysorbate 80. In various embodiments, low bioavailability fenofibrate-containing beads (slow beads) may be prepared using a different surfactant from high bioavailability fenofibrate-containing beads (fast beads). In various embodiments, the slow beads include from 0% to about 0.25% by weight of a surfactant, preferably from 0% to about 0.05% by weight of a surfactant, more preferably 0% by weight of a surfactant. In various embodiments, the fast beads include from about 0.3% to about 10% by weight of a surfactant, preferably from 0.3% to about 5% by weight of a surfactant, more preferably from about 0.5% to about 2% by weight of a surfactant.

In various embodiments, the slow beads contain between about 30% and about 80% micronized fenofibrate, relative to the total weight of the slow beads. Preferably, the slow beads contain between about 40% and about 59% micronized fenofibrate, more preferably between about 45% and about 55% micronized fenofibrate. The beads may contain between about 30% and about 59% micronized fenofibrate, relative to the total weight of the slow beads. Preferably, the fast beads contain between about 40% and about 59% micronized fenofibrate, more preferably between about 45% and about 55% micronized fenofibrate.

The fast beads disclosed herein contain fenofibrate and a binder in a ratio of fenofibrate:binder of from about 1:1 to less than 5:1, preferably from about 2:1 to about 4.5:1, more preferably from about 3.5:1 to about 4.5:1. In various embodiments, the binder is HPMC. In various embodiments, the fast beads disclosed herein contain fenofibrate and HPMC in a ratio of fenofibrate:HPMC of about 4:1. In some embodiments, the fast beads additionally comprise from 0.3% to about 10% by weight of sodium lauryl sulfate, preferably from 0.5% to about 2% by weight of sodium lauryl sulfate.

The slow beads disclosed herein contain fenofibrate and a binder in a ratio of fenofibrate:binder of from greater than 5:1 to about 15:1, preferably from about 6:1 to about 12:1, more preferably from about 7:1 to about 9:1. In various embodiments, the binder is HPMC, and the slow beads contain fenofibrate and HPMC in a ratio of fenofibrate:HPMC of about 8:1. In some embodiments, the slow beads additionally comprise from 0% to about 0.25% by weight of sodium lauryl sulfate, and are preferably free of sodium lauryl sulfate.

Fenofibrate, which is a prodrug of fenofibric acid, may be used as a micronized fenofibrate powder. The fenofibrate powder may be fenofibrate Form I as disclosed in U.S. Patent Publication 2009/0149533; fenofibrate Form II as disclosed in U.S. Patent Publication 2009/0149533; amorphous fenofibrate; hydrates or solvates of fenofibrate, or a mixture thereof. Fenofibrate may be partially or completely replaced with fenofibric acid; pharmaceutically acceptable salts of fenofibric acid; C1 to C5 esters or prodrugs of fenofibric acid, or a mixture thereof.

In various embodiments, the fast and slow beads are made using micronized fenofibrate with a weight-average particle diameter (D50) of between 1 and 15 microns, preferably between 4 and 10 microns. Preferably, the fast and slow beads are made using micronized fenofibrate where at least 99% of the fenofibrate particles have a particle diameter of less than 50 microns.

Various embodiments will be described in the following non-limiting examples. In the following examples, sugar spheres were used as the base substrate onto which the drug suspension was sprayed. The drug suspension was sprayed onto the sugar spheres in a fluidized bed fitted with a ROTOR Insert. The sugar spheres had a 20-25 mesh particle size distribution, providing a uniform surface area for drug layering.

The micronized fenofibrate used in the following examples had a weight average particle size D50 of between 5 and 7 microns, with at least 99% of particles having a particle size of <50 microns (D99); at least 90% of particles having a particle size of <15 microns (D90); and no more than 10% of particles having a particle size of <1 micron (D10).

Purified water was selected as a solvent for preparation of the drug suspension, as it provides a suitable medium for dissolving the hypromellose binder and suspending the micronized fenofibrate drug substance.

Hypromellose (Pharmacoat® 603) was used as a binder in the drug suspension, as it aids in adhering the drug to the sugar sphere substrate during processing. Sodium lauryl sulfate (SLS) was used as a surfactant in preparing the fast beads. Sodium lauryl sulfate is a commonly used excipient in solid oral dosage forms to enhance wetting and improve drug dissolution rate. This excipient is employed to enhance the aqueous wettability of fenofibrate in the drug layering suspension and to enhance the drug release from the high bioavailability, or fast, drug layered beads. Sodium lauryl sulfate was not used in the slow beads in the following examples, resulting in reduced drug release from the slow beads.

Simethicone, an antifoaming agent, was incorporated in the drug suspension to minimize the potential to generate foam during preparation of the drug layering suspension.

Approximately 0.1% w/w micronized talc was blended with the Fenofibrate Intermediate Beads, Type B prior to encapsulation to dissipate static charge and ensure efficient filling during encapsulation.

In various examples discussed below, formulations disclosed herein were administered to healthy adult volunteers in bioequivalence studies under fasting and fed conditions. The bioavailability achieved with the formulations disclosed herein is comparable to the bioavailability achieved with the administration of Lupin's ANTARA® capsules, where the ANTARA® capsules contain a single population of granules having a defined concentration of fenofibrate. The formulations disclosed herein include two populations of fenofibrate beads, including fast beads which have a higher bioavailability than the beads in ANTARA® capsules, and slow beads which have a lower bioavailability than the beads in ANTARA® capsules.

Manufacturing Process:

The manufacture of Fenofibrate Intermediate Beads or Pellets or Particles involves: Drug Suspension Manufacturing⇒ Rotor Drug Layering⇒ Fluid Bed Drying⇒ Screening Via Mesh⇒ Final Blending. The manufacturing process was shown to provide Fenofibrate Intermediate Beads with acceptable assay and content uniformity characteristics.

Manufacture of Fenofibrate Capsules (Micronized) proceeds via encapsulation of Fenofibrate Intermediate Beads blend using two separate capsule filling stations. Filling station I is used to encapsulate the Fast Fenofibrate Intermediate Beads and the Filling station II is used to encapsulate the Slow Fenofibrate Intermediate Beads. The manufacturing process was shown to provide a finished product with acceptable assay and content uniformity characteristics.

Drug Layer Suspension Manufacturing:

The drug layer suspension in this invention is manufactured using a high speed homogenizer mixer (Ross Model HSM 105, attached with a rotor/stator mixing blade used for the large scale manufacturing). During experimentation, several different types of mixer/disperser mixing head attachments were evaluated: slotted rotor/stator disperser, saw tooth disperser, slotted stator, and a fine screen stator with slotted disperser. Table 1 summarizes the formulation compositions and the drug release characteristics from these experiments. All formulations processed well and their drug release characteristics were similar, indicating that mixer type has no impact on formulation performance. Based on this evaluation, the rotor/stator configuration was chosen for the manufacture of the drug layering suspension. In addition, the process requires the suspension to be mixed with a homogenizer mixer for a minimum of 8 hours prior to drug layering, with continuous agitation of the suspension maintained throughout the drug layering process. The homogenization time minimum of 8 hours can be further reduced, based on processing efficiency.

TABLE 1

Fenofibrate Capsules USP, 130 mg
Evaluation of Homogenizer Mixing Head

|  | Slotted Rotor/Stator | | Saw tooth | | Slotted Stator | | Fine screen stator w/dispersator | |
| --- | --- | --- | --- | --- | --- | --- | --- | --- |
|  | X07-047-58A4 | % | X07-047-58A5 | % | X07-047-58A6 | % | X07-047-58A7 | % |
| Part I | | | | | | | | |
| Sugar Spheres (#35-#45) | 279.5 | 62.1 | 279.5 | 62.1 | 279.5 | 62.1 | 279.5 | 62.1 |
| Part II | | | | | | | | |
| Fenofibrate (Micronized) | 130.0 | 28.9 | 130.0 | 28.9 | 130.0 | 28.9 | 130.0 | 28.9 |
| Sodium Lauryl Sulfate | 9.0 | 2.00 | 9.0 | 2.00 | 9.0 | 2.00 | 9.0 | 2.00 |
| Pharmacoat 603 (Hypromellose) | 31.5 | 7.0 | 31.5 | 7.0 | 31.5 | 7.0 | 31.5 | 7.0 |
| Purified Water* | (682.0) | | (682.0) | | (682.0) | | (682.0) | |
| Total | 450.0 | | 450.0 | | 450.0 | | 450.0 | |

| Antara ® 130 mg | Dissolution condition: 1000 mL purified water, 0.01M sodium lauryl sulfate, USP Apparatus 2, at 75 rpm | | | | |
| --- | --- | --- | --- | --- | --- |
| Time | 0.01M SLS | 0.01M SLS | 0.01M SLS | 0.01M SLS | 0.01M SLS |
| 10 min | 21% | 19% | 21% | 21% | 19% |
| 15 min | 24% | 19% | 21% | 21% | 18% |
| 20 min | 24% | 19% | 21% | 21% | 18% |
| 30 min | 24% | 18% | 21% | 21% | 18% |
| 40 min | 24% | 18% | 21% | 21% | 18% |
| 60 min | 24% | 18% | 21% | 21% | 18% |

*Purified water removed during processing

Description of Rotor Drug Layering Process:

The fluidization pattern in the rotor processor can be best characterized as a spiraling helix. Three factors act on the beads or pellets or particles (materials) to produce this flow pattern. The rotating disk of the ROTOR insert provides centrifugal force which forces the rotating materials toward the wall of the processing chamber at the periphery of the rotor insert, while conditioned upward airflow through the rotor gap develops a vertical force causing the materials to become fluidized. The fluidization air pushes the moving materials upward into the expansion chamber until gravity overcomes the upward air velocity and the material falls toward the center of the disk where there is little air movement. The drug layer suspension is sprayed tangentially onto the rotating particles, while heated process air causes the applied drug layer suspension to dry before the particles move again into the spraying zone. This cyclical process is repeated many hundreds of times until the appropriate quantity of solids are applied to the rotating core substrate (material).

The efficiency of the drug layering process is dependent on the relationship between particle movement within the processor, drug layering suspension spray rate and the rate of solvent evaporation. The movement of the particles during rotor drug layering process is dependent on rotor speed and air flow. Rotor speed is considered a critical parameter since it can affect the integrity of the beads. Slow speeds can lead to product agglomeration while excessive speeds can cause attrition. Rotor speed is adjusted to maintain proper particle movement as the weight of the batch increases during drug layering process. Once proper movement of the particle bed is established, the deposition of drug layering solids onto the core substrate is controlled by the rate at which drug layering suspension is applied to core beads or pellets, and the rate at which solvent is removed from the system. The example of appropriate process parameters (inlet air temperature, product temperature, air flow, spray rate, nozzle atomizing air pressure, nozzle size and Rotor speed) utilized for manufacturing the beads in large scale batches utilizing FL-Multi-60 with a Rotogranulator Insert are summarized in the following Table 2.

TABLE 2

Rotor drug layering Process Parameters for manufacturing the beads or pellets or particles using a 30" rotor inserted with a FL-Multi-60 Fluid Bed Dryer. Batch Size: 50 kg

|  | Example 4 | | Example 6 | Example 7 | |
| --- | --- | --- | --- | --- | --- |
|  | R&D-I1976 | R&D-I1975 | R&D-I2052 | R&D-I2133 | R&D-I2128 |
| Inlet Temperature (° C.) | 50-65 | 54-65 | 53-64 | 52-67 | 56-69 |
| Product Temperature (° C.) | 31-34 | 30-35 | 30-32 | 34-32 | 36-36 |
| Air Flow (CFM) | 509-672 | 507-671 | 503-660 | 503-674 | 499-652 |
| Rotor Speed (rpm) | 100-125 | 100-125 | 100-125 | 99-125 | 100-125 |
| Rotor Gap | 4.0-6.0 | 4.0-6.0 | 4.0-6.0 | 4.0-6.5 | 4.0-6.0 |
| Atomization Air Pressure (psi) | 55 | 55 | 55 | 55 | 55 |
| Spray Rate (g/min) | 107-267 | 100-267 | 100-267 | 87-287 | 93-273 |
| Spray Nozzle Tip Size (mm) | 1.2 | 1.2 | 1.2 | 1.2 | 1.2 |

Example 1

Two formulations of fenofibrate containing beads were prepared. Each formulation was prepared by spraying a fenofibrate suspension onto sugar spheres having a size of 35 to 45 mesh in a fluidized bed. In one formulation (designated X07-047-58A1), the drug suspension included fenofibrate and HPMC in a ratio of 4:1, while in the other formulation (designated X07-047-62A 1), the drug suspension included fenofibrate and HPMC in a ratio of 2.4:1 were evaluated. The amounts of the various ingredients are set forth in Table 3 below. The bead formulations are prepared in a fluidized bed by spraying a water-based suspension of micronized fenofibrate, HPMC, and sodium lauryl sulfate onto the sugar spheres.

TABLE 3

Fenofibrate Capsules USP, 130 mg
(Compositions containing 7% w/w or
12% w/w Pharmacoat 603 as a binder)

|  | X07-047-58A1 (7% Pharmacoat 603) | | X07-047-62A1 (12% Pharmacoat 603) | |
| --- | --- | --- | --- | --- |
|  | mg | % | mg | % |
| Part I |  |  |  |  |
| Sugar Spheres (35-45 mesh) | 279.5 | 62.1 | 257.0 | 57.1 |
| Part II |  |  |  |  |
| Fenofibrate Jet Milled (Micronized) | 130.0 | 28.9 | 130.0 | 28.9 |
| Sodium Lauryl Sulfate | 9.0 | 2.0 | 9.0 | 2.0 |
| Pharmacoat 603 (HPMC, Hypromellose) | 31.5 | 7.0 | 54.0 | 12.0 |
| Purified Water* | (682.0) |  | (956.0) |  |
| Total | 450.0 |  | 450.0 |  |

*Removed during processing and does not contribute to the dry weight.

TABLE 4

Dissolution of Fenofibrate Capsules USP
Dissolution condition: 1000 mL purified water, 0.01M
Sodium Lauryl Sulfate (SLS), USP Apparatus 2, at 75 rpm

| Time | ANTARA® 0.01M SLS | X07-047-58A1 0.01M SLS | X07-047-62A1 0.01M SLS |
| --- | --- | --- | --- |
| 10 min | 21% | 21% | 20% |
| 15 min | 24% | 21% | 20% |
| 20 min | 24% | 21% | 20% |
| 30 min | 24% | 21% | 19% |
| 40 min | 24% | 21% | 19% |
| 60 min | 24% | 21% | 19% |

The formulation with 7% HPMC and the branded product ANTARA® yielded similar drug release characteristics in 1000 mL purified water containing 0.01M sodium lauryl sulfate, USP Apparatus 2, at 75 rpm, as seen in Table 4.

Example 2

The effect of a nonionic surfactant or wetting agent on the formulation was studied by evaluating the in vitro drug release characteristics of capsules containing beads. In these formulations, the drug to binder (Fenofibrate:HPMC) ratio was kept constant at 4:1, as seen in Table 5 below. The X07-047-64A1 was formulated without any surfactant, whereas the X07-047-65A1 was formulated with 2% Polysorbate 80. These formulations were manufactured by mixing micronized fenofibrate, HPMC, and Polysorbate 80 in water to form a drug suspension, and spraying the drug layer suspension onto the 35-45 mesh sugar spheres in a fluidized bed dryer inserted with a ROTOR.

TABLE 5

Fenofibrate Capsules USP, 130 mg - Compositions
Effect of a non-ionic surfactant, Polysorbate 80

|  | X07-047-64A1 7% Pharmacoat, No Surfactant | | X07-047-65A1 7% Pharmacoat, 2% Polysorbate 80 | |
| --- | --- | --- | --- | --- |
|  | mg | % | mg | % |
| Part I |  |  |  |  |
| Sugar Spheres (35-45 mesh) | 288.5 | 64.1 | 279.5 | 62.1 |
| Part II |  |  |  |  |
| Fenofibrate Jet Milled (Micronized) | 130.0 | 28.9 | 130.0 | 28.9 |
| Polysorbate 80 | 0.0 | 0.0 | 9.0 | 2.0 |
| Pharmacoat 603 (Hypromellose) | 31.5 | 7.0 | 31.5 | 7.0 |
| Purified Water | (682.0) |  | (682.0) |  |
| Total | 450.0 |  | 450.0 |  |

TABLE 6

Dissolution of Fenofibrate Capsules USP
Dissolution condition: 1000 mL purified water, 0.01M
sodium lauryl sulfate, USP Apparatus 2, at 75 rpm

| Time | ANTARA 0.01M SLS | X07-047-64A1 0.01M SLS | X07-047-65A1 0.01M SLS |
| --- | --- | --- | --- |
| 10 min | 21% | 21% | 20% |
| 15 min | 24% | 21% | 20% |
| 20 min | 24% | 21% | 20% |
| 30 min | 24% | 20% | 20% |
| 40 min | 24% | 20% | 20% |
| 60 min | 24% | 20% | 20% |

The formulations with 7% HPMC yielded similar drug release characteristics in 1000 mL purified water containing 0.01M sodium lauryl sulfate, USP Apparatus 2, at 75 rpm, to the drug release characteristics of the branded product ANTARA®, as seen in Table 6. This result was seen regardless of the presence or absence of a nonionic surfactant.

Example 3

A formulation containing fenofibrate and HPMC in a ratio of 4:1 was evaluated. The formulation additionally contained 2%, by weight of the formulation, of the anionic surfactant SLS, as seen in Table 7. A drug suspension containing micronized fenofibrate, HPMC (hypromellose, Pharmacoat 603), sodium lauryl sulfate, and the antifoaming agent simethicone, a mixture of polydimethylsiloxane and hydrated silica gel, was prepared in purified water, and sprayed onto 35-45 mesh sugar spheres in a large scale fluid bed dryer (FL-M-60) equipped with a rotor granulator insert to produce the drug layered intermediate beads. Simethicone was incorporated to the drug layering suspension at a low level (0.044% w/w) to minimize foaming during preparation. Following drug layering, the dried beads were blended with micronized talc, screened to remove agglomerates, and machine encapsulated into the two piece hard gelatin capsules (size #0EL). Table 7 presents a summary of the composition.

TABLE 7

Fenofibrate Capsules USP, 130 mg (Lot 1000317) Composition
(Contains Fenofibrate Intermediate Beads: 2% SLS, 4:1 Drug:HPMC)

|  | mg/g | % |
|---|---|---|
| Part I (Drug Layer Suspension) | | |
| Fenofibrate Micronized Intermediate | 130.0 | 28.87 |
| Hypromellose 2910 (Pharmacoat 603) | 31.5 | 7.0 |
| Sodium Lauryl Sulfate (Empicol LX/N) | 9.0 | 2.0 |
| Simethicone | 0.198 | 0.044 |
| Purified Water, USP | (342.0) | |
| Part II | | |
| Sugar Spheres (35/45 mesh) | 279.297 | 62.035 |
| Total | 450.0 | |
| Talc, Micronized | 0.225 | 0.05 |
| Total | 450.22 | |

The in vitro drug release of the above formulation was evaluated in a 1000 mL purified water containing 0.05 M SLS using USP Apparatus II at 75 rpm. Table 8 below summarizes the dissolution characteristics.

TABLE 8

Fenofibrate Capsules USP, 130 mg (Lot 1000317)
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B080033 | 54% | 74% | 84% | 93% | 97% | 100% |
| Fenofibrate Capsules, 130 mg #1000317 | 54% | 69% | 78% | 92% | 99% | 101% |

As seen in Table 8 above, the drug release rate of the formulation set forth in Table 7 (2% SLS, 4:1 Drug:HPMC) is comparable to the drug release rate of the branded product ANTARA®. Both formulations release 54% of the incorporated fenofibrate in 10 minutes; 92% to 93% of the incorporated fenofibrate in 30 minutes; and substantially all of the incorporated fenofibrate in 60 minutes.

The formulation of Table 7 was assessed in a pilot bioequivalence study, and compared to ANTARA® Capsules. Both the formulation of Table 7 and the ANTARA® Capsules contained 130 mg fenofibrate. The pilot bioequivalence study was an open-label, single-dose, randomized, two-period, two-treatment crossover study, using 24 normal healthy subjects. A summary of the pharmacokinetic data is presented in Table 9.

The FDA has provided guidance for bioequivalence between a branded product and a generic equivalent. In general, bioequivalence depends on several natural log transformed parameters associated with the rate and extent of absorption. Specifically, the entire 90% confidence interval for the ratio of the test to reference area under the curve from zero to the last detectable concentration, AUCL, must fall between 80 and 125% of the corresponding AUCL of the branded product for therapeutic equivalence. Additionally, the entire 90% confidence interval for the ratio of the test to reference maximum plasma concentration, Cpeak, must also fall between 80 and 125% of the corresponding Cpeak of the branded product for therapeutic equivalence to be declared.

The results of Table 9 indicate that the formulation of Table 7 exhibited a similar extent of absorption (AUCL) compared to ANTARA® capsules, but showed elevated drug concentration in the plasma. The 90% confidence interval for the AUCL is 104.6-115.5%, which falls within the FDA's desired confidence interval ratio of 80%-125%.

However, the Cpeak parameter for the formulation of Table 7 is 138% of the corresponding value for the branded product, with a 90% confidence interval of 128.1%-155%. This result falls outside the FDA's desired confidence interval ratio of 80%-125%. Accordingly, the formulation of Table 7 exhibits higher bioavailability under fasting conditions than the reference product ANTARA®. In this in vivo evaluation, the formulation of Table 7 used smaller size beads (35-45 mesh) than ANTARA® capsules, which might have caused increased bioavailability due to larger surface area of the dosage forms.

Example 4

Two different formulations containing 0.5% w/w sodium lauryl sulfate as a surfactant or 2% w/w sodium lauryl sulfate were manufactured. Both formulations contained fenofibrate and HPMC in a 4:1 ratio, as seen in Table 10. A drug suspension containing micronized fenofibrate, with a mean particle size of 10 microns, HPMC (hypromellose, Pharmacoat 603), sodium lauryl sulfate, and the antifoaming agent simethicone, a mixture of polydimethylsiloxane and hydrated silica gel, was prepared in purified water, and sprayed onto 20-25 mesh sugar spheres in a large scale fluid bed dryer (FL-M-60) equipped with a rotor granulator insert to produce the drug layered intermediate beads. A ratio of 4:1 fenofibrate to HPMC was used in the following formulations. Following the drug layering, the dried beads were blended with micronized talc, screened to remove the agglomerates and machine encapsulated using two piece hard gelatin capsules (size #0EL).

TABLE 9

Fenofibrate Capsules USP, 130 mg (Lot 1000317)
Initial Pilot Bioequivalence Study Results - Fasting (n = 24) Conditions, Study (FENO-08254)

| | Fenofibric Acid - AUCL | | | | Fenofibric Acid - CPEAK | | | | |
|---|---|---|---|---|---|---|---|---|---|
| Lot # | Mean (ng·hr/mL) | Ratio (M/I) | 90% CI | Intra subject % CV | Mean ng/mL | Ratio (M/I) | 90% CI | Intra subject % CV | Tpeak (hours) |
| 1000317 | 141825 | 1.10 | 104.6-115.5 | 10 | 6549.0 | 1.41 | 128.1-154.9 | 19.3 | 3.45 |
| B08003-ANTARA | 127830 | | | | 4740.0 | | | | 4.13 |

TABLE 10

Fenofibrate Capsules USP, 130 mg, #1000374
Fenofibrate Intermediate Beads (520.0 mg/gram), Lot#R&D-I1976, 2% SLS, 4:1 Drug:Pharmacoat 603
Fenofibrate Capsules USP, 130 mg, #1000375
Fenofibrate Intermediate Beads (520.0 mg/gram), Lot#R&D-I1975, 0.5% SLS, 4:1 Drug:Pharmacoat 603

| | Fenofibrate Capsules, 130 mg | | | | Fenofibrate Capsules, 130 mg | | | |
|---|---|---|---|---|---|---|---|---|
| | #1000374 Fenofibrate Intermediate R&D-I1976, 2% SLS, 4:1 Drug:HPMC | | Fenofibrate Capsules, 130 mg, #1000374 | | #1000375 Fenofibrate Intermediate R&D-I1975, 0.5% SLS, 4:1 Drug:HPMC | | Fenofibrate Capsules, 130 mg, #1000375 | |
| | mg/g | % | mg/capsule | % | mg/g | % | mg/capsule | % |
| Part I-Drug Layer Suspension | | | | | | | | |
| Fenofibrate Micronized | 520.0 | 52.0 | 130.0 | 51.95 | 520.0 | 52.0 | 130.0 | 51.95 |
| Pharmacoat 603 (Hypromellose) | 126.0 | 12.6 | 31.5 | 12.6 | 126.0 | 12.6 | 31.5 | 12.6 |
| Sodium Lauryl Sulfate | 20.0 | 2.0 | 5.0 | 2.0 | 5.0 | 0.5 | 1.25 | 0.5 |
| Simethicone | 0.22 | 0.022 | 0.055 | 0.022 | 0.22 | 0.022 | 0.055 | 0.022 |
| Purified Water* | (2735.0) | | | | (2735.0) | | | |
| Part II | | | | | | | | |
| Sugar Spheres (20/25 mesh) | 333.78 | 33.378 | 83.445 | 33.348 | 348.78 | 34.878 | 87.195 | 34.85 |
| Total | 1000.0 | 100 | 250.0 | | 1000.0 | 100 | 250.0 | |
| Talc, micronized | | | 0.225 | 0.0899 | | | 0.225 | 0.0899 |
| Total Fill Weight | | | 250.225 | | | | 250.225 | |

*Removed during processing

The in vitro drug release of the above formulation was evaluated in a 1000 mL purified water containing 0.05 M sodium lauryl sulfate using USP Apparatus II at 75 rpm. Table 11 summarizes the dissolution characteristics.

As seen in Table 11 below, the drug release rate of the formulations set forth in Table 10 is faster than the drug release rate of the branded product ANTARA®. Formulation #1000374, containing 2% sodium lauryl sulfate, releases 64% of the incorporated fenofibrate in 10 minutes; and substantially all of the incorporated fenofibrate in 30 minutes. ANTARA®, in contrast, releases 54% of the incorporated fenofibrate in 10 minutes; and 93% of the incorporated fenofibrate in 30 minutes. Formulation #1000375, containing 0.5% sodium lauryl sulfate, is more closely comparable to ANTARA® capsules, releasing 61% of the incorporated fenofibrate in 10 minutes; 94% of the incorporated fenofibrate in 30 minutes; and substantially all of the incorporated fenofibrate in 60 minutes.

TABLE 11

Fenofibrate Capsules USP, 130 mg
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B08003 | 54% | 74% | 84% | 93% | 97% | 100% |
| Fenofibrate Capsules, 130 mg #1000374 | 64% | 85% | 94% | 100% | 102% | 103% |
| Fenofibrate Capsules, 130 mg #1000375 | 61% | 77% | 86% | 94% | 98% | 102% |

The above formulations were assessed against the reference listed drug product in two separate pilot bioequivalence studies versus ANTARA® 130 mg Capsules (B08003), under fasting conditions in open-label, single-dose, randomized, two-period, two-treatment crossover studies initiated with 28 normal healthy adult subjects each. The methodology was similar to the methodology used in Example 3. Summaries of the pharmacokinetic data from these studies are presented in Tables 12 and 13. FIGS. 1 and 2 present the pharmacokinetic profile of the formulations in Table 10.

TABLE 12

Fenofibrate Capsules USP, 130 mg
Pilot Bioequivalence Study Results - Fasting (n = 28) Conditions
Study (FENO-0968)
(Formulation containing drug layered beads manufactured
with 2% sodium lauryl sulfate, #20-#25 Sugar Spheres, Drug:Pharmacoat 603, 4:1)

| Lot #<br>Brand | Fenofibric Acid - AUCL | | | | | Fenofibric Acid - CPEAK | | | | | Tpeak<br>(hours) |
|---|---|---|---|---|---|---|---|---|---|---|---|
| | Mean<br>(ng · hr/<br>mL) | %<br>CV | Ratio<br>(M/I) | 90%<br>CI | Intra<br>subject<br>% CV | Mean<br>ng/mL | %<br>CV | Ratio<br>(M/I) | 90%<br>CI | Intra<br>subject<br>% CV | |
| 1000374 | 125054 | 27.9 | 1.09 | 105-113 | 8% | 5428.7 | 35.3 | 1.28 | 119-138 | 16% | 4.0<br>(2-6) |
| B08003 | 114849 | 26.9 | | | | 4191.0 | 31.4 | | | | 5.0<br>(2-6) |

TABLE 13

Fenofibrate Capsules USP, 130 mg
Pilot Bioequivalence Study Results - Fasting (n = 25) Conditions
Study (FENO-0969)
(Formulation containing drug layered beads manufactured with 0.5% sodium lauryl sulfate,
20-#25 Sugar Spheres, Drug:Pharmacoat 603, 4:1)

| Lot #<br>Brand | Fenofibric Acid - AUCL | | | | | Fenofibric Acid - CPEAK | | | | | Tpeak<br>(hours) |
|---|---|---|---|---|---|---|---|---|---|---|---|
| | Mean<br>(ng · hr/<br>mL) | %<br>CV | Ratio<br>(M/I) | 90%<br>CI | Intra<br>subject<br>% CV | Mean<br>ng/mL | %<br>CV | Ratio<br>(M/I) | 90%<br>CI | Intra<br>subject<br>% CV | |
| 1000375 | 123828 | 35.8 | 1.12 | 107-117 | 9% | 4969 | 28.5 | 1.22 | 111-135 | 21% | 4.4<br>(2-9) |
| B08003 | 110477 | 33.6 | | | | 4099 | 34.8 | | | | 4.5<br>(2-10) |

The results of Table 12 indicate that Formulation #1000374, containing 2% sodium lauryl sulfate, exhibited a similar extent of absorption (AUCL) compared to ANTARA® capsules, but showed elevated drug concentration in the plasma. The 90% confidence interval for the AUCL is 105-113%, which falls within the FDA's desired confidence interval ratio of 80%-125%. However, the Cpeak parameter for Formulation #1000374 has a 90% confidence interval of 119-138%. This result falls outside the FDA's desired confidence interval ratio of 80%-125%.

The results of Table 13 indicate that the Formulation #1000375, containing 0.5% sodium lauryl sulfate, also exhibited elevated drug concentration in the plasma, compared to ANTARA® capsules. The 90% confidence interval for the Cpeak parameter for Formulation #1000375 has a 90% confidence interval of 111-135%, falling outside the FDA's desired confidence interval ratio of 80%-125%.

The pharmacokinetic results presented in the above table show that these modified formulations (containing 20-25 mesh sugar spheres as inert cores and 0.5 to 2% sodium lauryl sulfate) showed higher bioavailability than the reference product ANTARA®.

Example 5

On the basis of the bioavailability study results of Examples 3 and 4, sodium lauryl sulfate was removed from the formulation and the effect of three different binder concentrations of Pharmacoat 603 (4.3% w/w, 6.5% w/w and 13.0% w/w) on the drug release was evaluated. A drug suspension containing micronized fenofibrate, HPMC (hypromellose, Pharmacoat 603), and the antifoaming agent simethicone was prepared in purified water, and sprayed onto 20-25 mesh sugar spheres in a fluid bed dryer (GPCG 3) equipped with a rotor granulator insert to produce the drug layered intermediate beads. The amount of fenofibrate was held constant at 130 mg/capsule, while the ratio of fenofibrate was varied between 4:1 and 12:1, as seen in Table 14.

TABLE 14

Fenofibrate Capsules USP, 130 mg
(Formulation composition without sodium lauryl sulfate)

| | X07-047-81A1<br>4:1<br>Drug:Pharmacoat<br>603<br>ratio,<br>13% Pharmacoat<br>603 | | X07-047-82A1<br>8:1,<br>Drug:Pharmacoat<br>603<br>ratio,<br>6.5% Pharmacoat<br>603 | | X07-047-83A1<br>12:1,<br>Drug:Pharmacoat<br>603<br>ratio,<br>4.3% Pharmacoat<br>603 | |
|---|---|---|---|---|---|---|
| | mg | % | mg | % | mg | % |
| Part I | | | | | | |
| Sugar Spheres (#20-#25) | 87.5 | 35.0 | 103.75 | 41.5 | 109.2 | 43.7 |

TABLE 14-continued

Fenofibrate Capsules USP, 130 mg
(Formulation composition without sodium lauryl sulfate)

|  | X07-047-81A1 4:1 Drug:Pharmacoat 603 ratio, 13% Pharmacoat 603 | | X07-047-82A1 8:1, Drug:Pharmacoat 603 ratio, 6.5% Pharmacoat 603 | | X07-047-83A1 12:1, Drug:Pharmacoat 603 ratio, 4.3% Pharmacoat 603 | |
|---|---|---|---|---|---|---|
|  | mg | % | mg | % | mg | % |
| Part II |  |  |  |  |  |  |
| Fenofibrate (Micronized) | 130.0 | 52.0 | 130.0 | 52.0 | 130.0 | 52.0 |
| Pharmacoat 603 (Hypromellose) | 32.5 | 13.0 | 16.25 | 6.5 | 10.8 | 4.3 |
| Purified Water* | (682.0) |  | (682.0) |  | (682.0) |  |
| Total | 250.0 |  | 250.0 |  | 250.0 |  |

*Removed during processing

The in vitro drug release of the formulations of Table 14 was evaluated in a 1000 mL purified water containing 0.025 M sodium lauryl sulfate using USP Apparatus II at 75 rpm. Table 15 summarizes the drug release characteristics, as seen in Table 15.

TABLE 15

Fenofibrate Capsules USP, 130 mg
Dissolution Condition: USP Apparatus II, 75 rpm, 1000 mL, 0.025M SLS

| Product | Drug:HPMC ratio | % HPMC | 10 min | 15 min | 20 min | 30 min | 40 min | 60 min |
|---|---|---|---|---|---|---|---|---|
| ANTARA ® Capsules, 130 mg; B08003 |  |  | 35% | 52% | 62% | 74% | 83% | 92% |
| Fenofibrate Capsules, 130 mg #X07-047-81A1 | 4:1 | 13% w/w | 72% | 80% | 95% | 97% | 98% | 99% |
| Fenofibrate Capsules, 130 mg #X07-047-82A1 | 8:1 | 6.5% w/w | 51% | 68% | 77% | 85% | 89% | 94% |
| Fenofibrate Capsules, 130 mg #X07-047-83A1 | 12:1 | 4.3% w/w | 18% | 28% | 38% | 49% | 57% | 66% |

The data presented in the above shows that higher concentrations of HPMC yielded more rapid drug release in formulations containing no sodium lauryl sulfate.

Example 6

Formulation X07-047-82A1 containing 6.5% w/w Pharmacoat 603 with no sodium lauryl sulfate was manufactured in a large scale equipment as lot 1000442 using Size#0EL capsules shell and evaluated in a bioequivalence study versus ANTARA® capsules. Table 16 describes this formulation.

TABLE 16

Fenofibrate Capsules, 130 mg, #1000442
(Contains drug layered beads manufactured without sodium lauryl sulfate (SLS), #20-#25 Sugar Spheres. 8:1 Drug:Pharmacoat 603)

|  | Fenofibrate Intermediate Beads, R&D-I 2052, 8:1 Drug:Pharmacoat 603 | | Fenofibrate Capsules USP, 130 mg, #1000442 | |
|---|---|---|---|---|
|  | mg/g | % | mg/capsule | % |
| Part I-A (Drug Layer Suspension) |  |  |  |  |
| Fenofibrate Micronized | 520.0 | 52.0 | 130.0 | 51.95324 |
| Hypromellose 2910 (Pharmacoat 603) | 65.0 | 6.5 | 16.25 | 6.5 |
| Simethicone | 0.22 | 0.022 | 0.055 | 0.02198 |
| Purified Water* Part-IB | (2735.0) |  |  |  |
| Sugar Spheres (20/25 mesh) | 414.78 | 41.478 | 103.695 | 41.4407 |
| Total | 1000.0 | 100 | 250.0 |  |
| Talc, micronized |  |  | 0.225 | 0.08991 |
| Total Fill Weight |  |  | 250.225 | 100.0 |

*Purified removed during processing

The in vitro drug release of the above formulation was evaluated in a 1000 mL purified water containing 0.05 M sodium lauryl sulfate using USP Apparatus II at 75 rpm. Table 17 below summarizes the drug release characteristics.

TABLE 17

Fenofibrate Capsules USP, 130 mg
Dissolution (USP Apparatus II, 75 rpm, 1000 mL, 0.05M SLS)

| Product | 10 min | 15 min | 20 min | 30 min | 40 min | 60 min |
|---|---|---|---|---|---|---|
| ANTARA ® Capsules, 130 mg; B08003 | 54% | 74% | 84% | 93% | 97% | 100% |
| Fenofibrate Capsules, 130 mg #1000442 | 14% | 23% | 35% | 62% | 78% | 88% |

As seen in Table 17, the capsules of Table 16 release the drug more slowly than the comparative ANTARA® capsules. After 10 minutes, the comparative ANTARA® capsules released 54% of the drug, while the capsules of Table 14 released only 14% of the drug. Additionally, the capsules of Table 14 were assessed in a bioequivalence study versus ANTARA® Capsules, 130 mg in an open-label, single-dose, randomized, two-period, two-treatment crossover study using 32 normal healthy subjects (27 completed the study). The methodology was similar to the methodology used in Example 3. A summary of the pharmacokinetic data from this study is presented in Table 18. Also, a plot showing pharmacokinetic profile is shown in FIG. 3.

TABLE 18

Fenofibrate Capsules USP, 130 mg (Lot 1000442)
Pilot Bioequivalence Study Results - Fasting (n = 27) Conditions
Study (FENO-09288)

| | Fenofibric Acid - AUCL | | | | | Fenofibric Acid - CPEAK | | | | | |
|---|---|---|---|---|---|---|---|---|---|---|---|
| Lot # Brand | Mean (ng · hr/mL) | % CV | Ratio (M/I) | 90% CI | Intra subject % CV | Mean ng/mL | % CV | Ratio (M/I) | 90% CI | Intra subject % CV | Tpeak (hours) |
| 1000442 | 76734 | 40.0 | 0.56 | 53-59 | 13% | 2263.4 | 31.8 | 0.49 | 45-53 | 18.0% | 5.0 (3-10) |
| B08003 | 134952 | 34.9 | | | | 4748.7 | 36.8 | | | | 4.0 (2-6) |

The capsules of Table 16 exhibited poor bioavailability under fasting conditions due to a low AUCL and Cpeak. The results of Table 18 indicate that the capsules of Table 16, containing fenofibrate and HPMC in a ratio of 8:1 and no sodium lauryl sulfate, exhibited low absorption (AUCL) compared to ANTARA® capsules. The capsules of Table 16 showed between 53% and 59%% of the absorption (AUCL) observed with the branded product, with a confidence interval of 90%. Additionally, the Cpeak parameter for capsules of Table 16 has a 90% confidence interval of 45% to 53% when compared to the branded product. This result falls outside the FDA's desired confidence interval ratio of 80%-125%, and indicates that the capsules of Table 16 are not bioequivalent to ANTARA® capsules.

Example 7

Three alternative intermediate bead formulations were scaled-up. The first group of beads, Fenofibrate Intermediate Beads, Type A, Lot #R&D-12133, contain 0.5% sodium lauryl sulfate. The second group of beads, Fenofibrate Intermediate Beads, Type B, Lot #R&D-12134, contain 2% sodium lauryl sulfate. The third group of beads, Fenofibrate Intermediate Beads, Type C, Lot #R&D-12128, contains no sodium lauryl sulfate.

Based on pharmacokinetic analysis, two capsule formulations containing different ratios of the above beads were machine encapsulated in size #0EL and dosed in a bioequivalence study. The first capsule formulation, lot #1000529, contained an 80:20 ratio of Type A beads and Type C beads, and the second capsule formulation, lot #1000530, contained a 75:25 ratio of Type B and Type C beads. Tables 19, 20, and 21 summarize these two capsule formulations and drug release characteristics.

TABLE 19

Fenofibrate Capsules USP, 130 mg, #1000529
(Contains 80% w/w Fenofibrate Intermediate Beads, Type A (0.5% SLS), Lot# R&D-I12133 and
20% w/w Fenofibrate Intermediate Beads, Type C (No SLS), Lot# R&D-I12128)

| | Fenofibrate Intermediate Beads Type A, 0.5% SLS, R&D-I2133 Drug:HPMC, 4:1 | | Fenofibrate Intermediate Beads Type C, No SLS, R&D-I2128, Drug:HPMC, 8:1 | | 80% w/w Type A Beads | 20% w/w Type C Beads | Fenofibrate Capsules USP, 130 mg, #1000529 80:20 | |
|---|---|---|---|---|---|---|---|---|
| | mg/g | % | mg/g | % | Mg | mg | mg | % |
| Part I-A (Drug Layer Suspension) | | | | | | | | |
| Fenofibrate Micronized | 520.0 | 52.0 | 520.0 | 52.0 | 104.0 | 26.0 | 130.0 | 51.95 |
| Hypromellose 2910 (Pharmacoat 603) | 126.0 | 12.6 | 65.0 | 6.5 | 25.2 | 3.25 | 28.45 | 11.37 |
| Sodium Lauryl Sulfate | 5.0 | 0.5 | | | 1.0 | | 1.0 | 0.4 |
| Simethicone | 0.22 | 0.022 | 0.22 | 0.022 | 0.044 | 0.011 | 0.055 | 0.022 |
| Purified Water* | (2735.0) | | (2735.0) | | | | | |
| Part-IB | | | | | | | | |
| Sugar Spheres (20/25 mesh) | 348.78 | 34.878 | 414.78 | 41.48 | 69.756 | 20.739 | 90.495 | 36.17 |
| Total | 1000.0 | 100 | 1000.0 | 100 | 200.0 | 50.0 | 250.0 | |
| Talc, micronized | | | | | 0.225 | — | 0.225 | 0.09 |
| Total Capsule Fill Wt. | | | | | | | 250.225 | |

*Removed during processing

TABLE 20

Fenofibrate Capsules USP, 130 mg, #1000530
(Contains 75% w/w Fenofibrate Intermediate Beads, Type B (2% SLS), Lot#R&D-I2134 and
25% w/w Fenofibrate Intermediate Beads, Type C (No SLS), Lot#R&D-I2128)

| | Fenofibrate Intermediate Beads Type B, 2% SLS, Drug:Pharmacoat, 4:1, R&D-I2134 | | Fenofibrate Intermediate Beads Type C, R&D-I2128, No SLS Drug:HPMC, 8:1 | | 75% w/w Type B Beads | 25% w/w Type C Beads | Fenofibrate Capsules USP, 130 mg, #1000530 75:25 | |
|---|---|---|---|---|---|---|---|---|
| | mg/g | % | mg/g | % | mg | mg | mg | % |
| Part I (Drug Layer Suspension) | | | | | | | | |
| Fenofibrate Micronized | 520.0 | 52.0 | 520.0 | 52.0 | 97.5 | 32.5 | 130.0 | 51.95 |
| Hypromellose 2910 (Pharmacoat 603) | 126.0 | 12.6 | 65.0 | 6.5 | 23.625 | 4.0625 | 27.6875 | 11.07 |
| SLS | 20.0 | 2.0 | NA | NA | 3.75 | | 3.75 | 1.5 |
| Simethicone | 0.22 | 0.022 | 0.22 | 0.022 | 0.04125 | 0.01375 | 0.055 | 0.22 |
| Purified Water* | (2735.0) | | (2735.0) | | | | | |
| Part II | | | | | | | | |
| Sugar Spheres (20/25 mesh) | 333.78 | 33.38 | 414.78 | 41.478 | 62.58375 | 25.92375 | 88.5075 | 35.37 |
| Total | 1000.0 | 1000.0 | 1000.0 | 100 | 187.5 | 62.5 | 250.0 | |
| Talc, micronized | | | | | 0.225 | | 0.225 | 0.09 |
| Total Capsule Fill Wt, mg | | | | | | | 250.225 | |

*Removed during processing

The drug release characteristics of the above two capsule formulations are evaluated using USP Apparatus II, 75 rpm, 1000 mL, 0.05 M SLS, and are summarized in Table 21. As seen in Table 21, the dissolution rate of the capsule formulations of Tables 19 and 20 is slower than the dissolution rate of ANTARA® capsules containing an equivalent amount of fenofibrate, i.e., 130 mg. Additionally, the drug release rate of the capsule formulations of Tables 19 and 20 is slower than a capsule prepared using the formulation of Table 14, containing fenofibrate and HPMC in a ratio of 8:1, with no sodium lauryl sulfate. The dissolution rate of the capsule formulations of Tables 19 and 20 is also substantially slower than a capsule prepared using Type B beads alone, where the Type B beads contain fenofibrate and HPMC in a ratio of 4.1:1, with 2% sodium lauryl sulfate.

TABLE 21

Fenofibrate Capsules USP, 130 mg
Dissolution Condition: USP Apparatus II, 75 rpm, 1000 mL, 0.05M SLS

| Product | 10 min | 15 min | 20 min | 30 min | 40 min | 60 min |
|---|---|---|---|---|---|---|
| ANTARA Capsules, 130 mg; B08017 | 49% | 73% | 84% | 94% | 97% | 100% |
| Fenofibrate Intermediate Beads, R&D I2052, Type C Beads | 63% | 78% | 84% | 90% | 93% | 97% |
| Fenofibrate Intermediate Beads, R&D I2134, Type B Beads | 92% | 98% | 100% | 100% | 100% | 100% |
| Fenofibrate Capsule, 130 mg, Lot. 1000529 | 33% | 50% | 64% | 79% | 88% | 96% |
| Fenofibrate Capsule, 130 mg, Lot. 1000530 | 45% | 60% | 68% | 78% | 85% | 93% |

The capsules of Table 16 were assessed in a bioequivalence study versus ANTARA® Capsules, 130 mg, in an open-label, single-dose, randomized, two-period, two-treatment crossover study using 21 normal healthy subjects. The methodology was similar to the methodology used in Example 3. A summary of the pharmacokinetic data from this study is presented in Table 22. A plot showing pharmacokinetic profile, specifically plasma levels, is shown in FIG. 4.

TABLE 22

Fenofibrate Capsules USP, 130 mg
Pilot Bioequivalence Study Results - Fasting
(n = 21) Conditions; Study (FENO-1018)
Treatment A: Lot 1000529 contains 80% Fast Beads (0.5% SLS) and 20% Slow Beads (No SLS); Dose: 1 × 130 mg
Treatment B: Lot 1000530 contains 75% Fast Beads (2% SLS) and 25% Slow Beads (No SLS); Dose: 1 × 130 mg
Treatment C: Antara Capsules, Lot: B08017; Dose: 1 × 130 mg; Oscient/Lupin

|  | Mean | Mean | 90% CI |
|---|---|---|---|
|  | Treatment A = Lot 1000529 | Treatment C = Lot B08017 |  |
| AUCI (ng · hr/mL) | 122189.62 | 124010.37 | 94-106 |
| AUCL (ng · hr/mL) | 113485.24 | 117167.45 | 92-105 |
| CPEAK (ng/mL) | 4498.10 | 4720.35 | 88-108 |
| TPEAK (Hour)* | 3.5 (2-10) | 4 (2-12) |  |
|  | Treatment B = Lot 1000530 | Treatment C = LotB08017 |  |
| AUCI (ng · hr/mL) | 116320.92 | 124010.37 | 90-102 |
| AUCL (ng · hr/mL) | 108823.93 | 117167.45 | 89-101 |
| CPEAK (ng/mL) | 4656.90 | 4720.35 | 90-109 |
| TPEAK (Hour)* | 4.0 (2.0-24) | 4 (2-12) |  |

*Median values, with range in parentheses.

The pharmacokinetic results presented in Table 22 demonstrate that the formulations of Tables 19 and 20 were each bioequivalent to ANTARA®. Formulation #1000529, containing 80% Type A beads and 20% Type C beads, exhibited an extent of absorption (AUCL) which was between 92% and 105% of the absorption observed with ANTARA® capsules, within a confidence interval of 90%. Formulation #1000530, containing 75% Type B beads and 25% Type C beads, exhibited an extent of absorption (AUCL) which was between 89% and 101% of the absorption observed with ANTARA® capsules, within a confidence interval of 90%. This result falls within the FDA's desired confidence interval ratio of 80%-125%.

Additionally, the Cpeak parameter for Formulation #1000529 was 88% to 108% of the Cpeak observed with ANTARA® capsules, within a confidence interval of 90%; and the Cpeak parameter for Formulation #1000530 was 90% to 109% of the Cpeak observed with ANTARA® capsules, within a confidence interval of 90%. This result falls within the FDA's desired confidence interval ratio of 80%-125%. The results of Table 22 indicate that the Formulation #1000529 and Formulation #1000530 are each bioequivalent to ANTARA® capsules.

Example 8

A large scale batch, Formulation #1000596 was manufactured using the Formulation composition of 1000530 (shown in Table 20). This capsule contains two different types of Fenofibrate Intermediate Beads, one containing no surfactant (Fenofibrate Intermediate Beads, Type C, 520 mg/g) and the other containing sodium lauryl sulfate as a surfactant (Fenofibrate Intermediate Beads, Type B). Each capsule contains 25% w/w Fenofibrate Intermediate Beads Type C (520 mg/g) and 75% w/w Fenofibrate Intermediate Beads Type B which corresponds to theoretical fill weights of 62.5 mg and 187.725 mg, respectively. The actual fill weight of each bead is adjusted based on the potency factor assigned to each bead prior to encapsulation. Each bead type was filled into the capsule shell using a separate dosing station during encapsulation.

The resulting Capsules USP, 130 mg (Lot. 100596) were dosed in a bioequivalence study versus the reference listed drug, ANTARA® Capsules, 130 mg. The study was a single dose, open label, randomized, 2-period, 2-treatment crossover of the test and reference products administered under fasting and post-prandial conditions. Statistical analyses of the data revealed that the 90% confidence intervals were within the acceptable bioequivalent range of 80% and 125% for the natural log transformed parameters AUCL, AUCI, and CPEAK for fenofibric acid. This study demonstrates that Capsules of Lot. 100596, 130 mg are bioequivalent to ANTARA® Capsules, 130 mg, following a single, oral 130 mg (1×130 mg capsule) dose administered under fasting and post-prandial conditions. A summary of the pharmacokinetic data from this study is presented in Table 23 and Table 24. FIG. 5 and FIG. 6 display the pharmacokinetic profile, specifically plasma concentration of fenofibrate over time, for Capsules of Lot. 100596, 130 mg which are bioequivalent to ANTARA® Capsules, 130 mg.

TABLE 23

Fenofibrate Capsules USP, 130 mg (Lot#1000596)
Bioequivalence Study Results - Fasting (n = 29) Conditions; Study (FENO-10202)
(Formulation 1000596 contains 75% Fast Beads (2% SLS Beads) and 25% Slow Beads (No SLS))

| | Fenofibric Acid - AUCL | | | | | Fenofibric Acid - CPEAK | | | | | |
| --- | --- | --- | --- | --- | --- | --- | --- | --- | --- | --- | --- |
| Lot # | Mean (ng · hr/mL) | % CV | Ratio (M/I) | 90% CI | Intra subject % CV | Mean ng/mL | % CV | Ratio (M/I) | 90% CI | Intra subject % CV | Tpeak (hours) |
| 100596 | 121040 | 36.5 | 0.97 | 92-102 | 11.5% | 4617 | 35 | 1.08 | 99-117 | 19% | 4.2 (2-10) |
| B08017 | 123455 | 34.4 | | | | 4321 | 39.4 | | | | 4.5 (2-10) |

TABLE 24

Fenofibrate Capsules USP, 130 mg (Lot#1000596)
Bioequivalence Study Results - Fed (Post-Prandial) (n = 31) Conditions; Study (FENO-10203)
(Formulation 1000596 contains 75% Fast Beads (2% SLS Beads) and 25% Slow Beads (No SLS))

| | Fenofibric Acid - AUCL | | | | | Fenofibric Acid - CPEAK | | | | | |
| --- | --- | --- | --- | --- | --- | --- | --- | --- | --- | --- | --- |
| Lot # | Mean (ng · hr/mL) | % CV | Ratio (M/I) | 90% CI | Intra subject % CV | Mean ng/mL | % CV | Ratio (M/I) | 90% CI | Intra subject % CV | Tpeak (hours) |
| 100596 | 140403 | 31.6 | 0.97 | 94-100 | 7.22% | 8300 | 17.8 | 0.996 | 96-104 | 10% | 5.7 (3-12) |
| B08017 | 145208 | 32 | | | | 8381 | 20.6 | | | | 6.1 (2-12) |

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A dosage form comprising a therapeutically effective amount of fenofibric acid, pharmaceutically acceptable salts thereof, pharmaceutically acceptable esters thereof, or prodrugs thereof, said dosage form comprising:
  a plurality of first granules and a plurality of second granules being combined in a weight ratio of said first granules to said second granules of between about 50:50 and about 90:10,
  wherein said dosage form provides a peak plasma concentration of fenofibric acid of between 4000 ng/mL and 4800 ng/mL when administered to a human subject;
  wherein a first comparative dosage form comprising 100% of first granules provides a peak plasma concentration of fenofibric acid of greater than 4800 ng/mL when administered to said human subject; and a second comparative dosage form comprising 100% of second granules provides a peak plasma concentration of fenofibric acid of less than 3500 ng/mL when administered to said human subject.

2. A dosage form comprising:
  a plurality of first granules, each of said first granules comprising a first inert core with a first coating thereon, said first coating comprising fenofibric acid, a pharmaceutically acceptable salt thereof, a pharmaceutically acceptable ester thereof, or a prodrug thereof; from 0.3% to 10% by weight of said first granules of a first surfactant; and a first water soluble or water dispersible cellulose derivative; and
  a plurality of second granules, each of said second granules comprising a second inert core with a second coating thereon, said second coating comprising fenofibric acid, a pharmaceutically acceptable salt thereof, a pharmaceutically acceptable ester thereof, or a prodrug thereof; from 0% to 0.25% by weight of said second granules of a second surfactant; and a second water soluble or water dispersible cellulose derivative;
  substantially all of said fenofibric acid, pharmaceutically acceptable salts thereof, pharmaceutically acceptable esters thereof, or prodrugs thereof being contained in said first coating and said second coating;
  said first granules and said second granules being combined in a weight ratio of said first granules to said second granules of between about 60:40 and about 90:10;
  wherein said dosage form provides a peak plasma concentration of fenofibric acid of between 4000 ng/mL and 4800 ng/mL when administered to a human subject;

wherein a first comparative dosage form comprising 100% of first granules provides a peak plasma concentration of fenofibric acid of greater than 4800 ng/mL when administered to said human subject; and a second comparative dosage form comprising 100% of second granules provides a peak plasma concentration of fenofibric acid of less than 3500 ng/mL when administered to said human subject.

3. The pharmaceutical composition of claim 2, wherein said first surfactant is the same as said second surfactant, and said first cellulose derivative is the same as said second cellulose derivative.

4. The pharmaceutical composition of claim 2, wherein said second composition contains 0% by weight of said second surfactant.

5. A pharmaceutical composition having a target bioavailability in vivo, said pharmaceutical composition comprising:
a plurality of first granules having a first bioavailability in vivo, each of said first granules comprising a first inert core with a first coating thereon, said first coating comprising fenofibric acid, a pharmaceutically acceptable salt thereof, a pharmaceutically acceptable ester thereof or a prodrug thereof; from 0.3% to 10% by weight of said first granules of a first surfactant; and a first water soluble or water dispersible cellulose derivative, and
a plurality of second granules having a second bioavailability in vivo, each of said second granules comprising a second inert core with a second coating thereon, said second coating comprising fenofibric acid, a pharmaceutically acceptable salt thereof, a pharmaceutically acceptable ester thereof, or a prodrug thereof; from 0.3% to 10% by weight of said first granules of a first surfactant; and a first water soluble or water dispersible cellulose derivative,
said target bioavailability being between said first bioavailability and said second bioavailability;
substantially all of said fenofibric acid, pharmaceutically acceptable salts thereof, pharmaceutically acceptable esters thereof, or prodrugs thereof being contained in said first coating and said second coating.

6. The pharmaceutical composition of claim 5, wherein said pharmaceutical composition comprises:
from 50% to 90% of said first granules, based on the combined weight of said first and second granules; and
from 10% to 50% of said second granules, based on the combined weight of said first and second granules.

7. The pharmaceutical composition of claim 5, wherein said first bioavailability in vivo is the bioavailability of a comparative dosage form comprising 100% of said first granules and 0% of said second granules; and
said second bioavailability in vivo is the bioavailability of a comparative dosage form comprising 0% of said first granules and 100% of said second granules.

8. The pharmaceutical composition of claim 5, wherein said first surfactant is the same as said second surfactant, and said first cellulose derivative is the same as said second cellulose derivative.

9. The pharmaceutical composition of claim 5, wherein said second composition contains 0% by weight of said second surfactant.

10. The immediate release pharmaceutical composition of claim 5, wherein at least one of said each first granule and said each second granule comprises an inert core.

11. An immediate release pharmaceutical composition comprising:
a plurality of first granules comprising fenofibrate, from 0.3% to 10% by weight of said first granules of a first surfactant, and a first water soluble or water dispersible cellulose derivative, wherein said first plurality of first granules releases fenofibrate at a first rate upon exposure to water, and
a plurality of second granules comprising fenofibrate, from 0% to 0.25% by weight of said second granules of a second surfactant, and a second water soluble or water dispersible cellulose derivative, wherein said plurality of second granules releases fenofibrate at a second rate upon exposure to water, said second rate being less than said first rate,
wherein each first granule and each second granule comprises an inert core;
substantially all of said fenofibrate being contained in said first granules and said second granules.

12. The immediate release pharmaceutical composition of claim 11, wherein:
each first granule comprises an inert core coated with a first composition comprising said fenofibrate, said first surfactant, and said first cellulose derivative; and
each second granule comprises an inert core coated with a second composition comprising said fenofibrate, said second surfactant, and said second cellulose derivative.

13. The immediate release pharmaceutical composition of claim 11, wherein:
said fenofibrate and said first cellulose derivative are present in said first granules in a weight ratio of from about 1:1 to less than 5:1; and wherein
said fenofibrate and said second cellulose derivative are present in said second granules in a weight ratio of from greater than 5:1 to about 15:1.

14. The immediate release pharmaceutical composition of claim 13, wherein said fenofibrate and said first cellulose derivative are present in said first granules in a weight ratio of from about 2:1 to about 4.5:1; and
wherein said fenofibrate and said second cellulose derivative are present in said second granules in a weight ratio of from about 6:1 to about 12:1.

15. The immediate release pharmaceutical composition of claim 14, wherein said fenofibrate and said first cellulose derivative are present in said first granules in a weight ratio of about 3.5:1 and about 4.5; and
wherein said fenofibrate and said second cellulose derivative are present in said second granules in a weight ratio of from about 7:1 to about 9:1.

16. The immediate release pharmaceutical composition of claim 11, wherein said first granules comprise from 30 to 59% by weight of the first granules fenofibrate; and
said second granules comprise from 30 to 59% by weight of the second granules fenofibrate.

17. The immediate release pharmaceutical composition of claim 16, wherein said first granules comprise from 40 to 55% by weight of the first granules fenofibrate; and
said second granules comprise from 40 to 55% by weight of the second granules fenofibrate.

18. A dosage form comprising a therapeutically effective amount of fenofibrate, said dosage form comprising:
a first composition and a second composition being combined in a weight ratio of said first composition to said second composition of between about 50:50 and about 90:10,
wherein said dosage form, when administered to a human subject, provides a peak plasma concentration Cpeak of fenofibric acid test to reference least squares mean ratio where the 90% confidence interval is between 80% and 125% of the natural log-transformed Cpeak value obtained with commercially available fenofibrate capsules having an amount of fenofibrate which is equal to said therapeutically effective amount;

wherein a first comparative dosage form comprising 100% of said first composition provides a Cpeak of fenofibric acid test to reference least squares mean ratio where the 90% confidence interval is between 105% and 160% of the natural log-transformed Cpeak value obtained with said commercially available fenofibrate capsules; and a second comparative dosage form comprising 100% of said second composition provides a Cpeak of fenofibric acid test to reference least squares mean ratio where the 90% confidence interval is less than 80% of the natural log-transformed Cpeak value obtained with said commercially available fenofibrate capsules.

19. The dosage form of claim 18, wherein:

said first comparative dosage form comprising 100% of said first composition provides a Cpeak of fenofibric acid test to reference least squares mean ratio where the 90% confidence interval is between 105% and 140% of the natural log-transformed Cpeak value obtained with said commercially available fenofibrate capsules; and a second comparative dosage form comprising 100% of said second composition provides a Cpeak of fenofibric acid test to reference least squares mean ratio where the 90% confidence interval is between 40% and 80% of the natural log-transformed Cpeak value obtained with said commercially available fenofibrate capsules.

20. The dosage form according to claim 19, wherein:

said dosage form, when administered to a human subject, provides a value of AUCL for fenofibric acid test to reference least squares mean ratio where the 90% confidence interval is between 80% and 125% of the natural-log transformed AUCL value obtained with said commercially available fenofibrate capsules, and a value of AUCI for fenofibric acid test to reference least squares mean ratio where the 90% confidence interval is between 80% and 125% of the natural-log transformed AUCI value obtained with said commercially available fenofibrate capsules.

* * * * *